United States Patent [19]

Cobb

[11] 3,956,356

[45] May 11, 1976

[54] CONVERSION OF LACTAMS TO ALKENENITRILES

[75] Inventor: Raymond L. Cobb, Bartlesville, Okla.

[73] Assignee: Phillips Petroleum Company, Bartlesville, Okla.

[22] Filed: Oct. 7, 1970

[21] Appl. No.: 78,753

[52] U.S. Cl. .............................. 260/465.2; 260/464; 260/465 B
[51] Int. Cl.² ...................................... C07C 120/10
[58] Field of Search .......... 260/465.2, 465.5, 465 B, 260/464, 465.9, 465.5 R

[56] References Cited
UNITED STATES PATENTS

| | | | |
|---|---|---|---|
| 2,830,072 | 4/1958 | Garritsen et al. ................. | 260/465.5 |
| 3,036,113 | 5/1962 | Ottenheym ...................... | 260/465.2 |
| 3,555,059 | 1/1971 | Schwarz et al. .................. | 260/465.2 |
| 3,567,757 | 3/1971 | Ida et al. ........................... | 260/465.2 |
| 3,579,588 | 5/1971 | Immel et al. ..................... | 260/465.2 |

*Primary Examiner*—Joseph P. Brust

[57] ABSTRACT

A process is provided for the conversion of lactams to the corresponding aminonitriles and alkenenitriles comprising contacting the lactam with ammonia in the presence of a catalyst in a first reaction zone to form the corresponding aminonitrile and a byproduct polymeric material, and contacting the byproduct in the presence of gamma-alumina, a second catalyst, in a second reaction zone to form the corresponding isomeric alkenenitriles. The aminonitrile and the alkenenitriles are both recovered as products of the process.

4 Claims, 1 Drawing Figure

U.S. Patent May 11, 1976 3,956,356
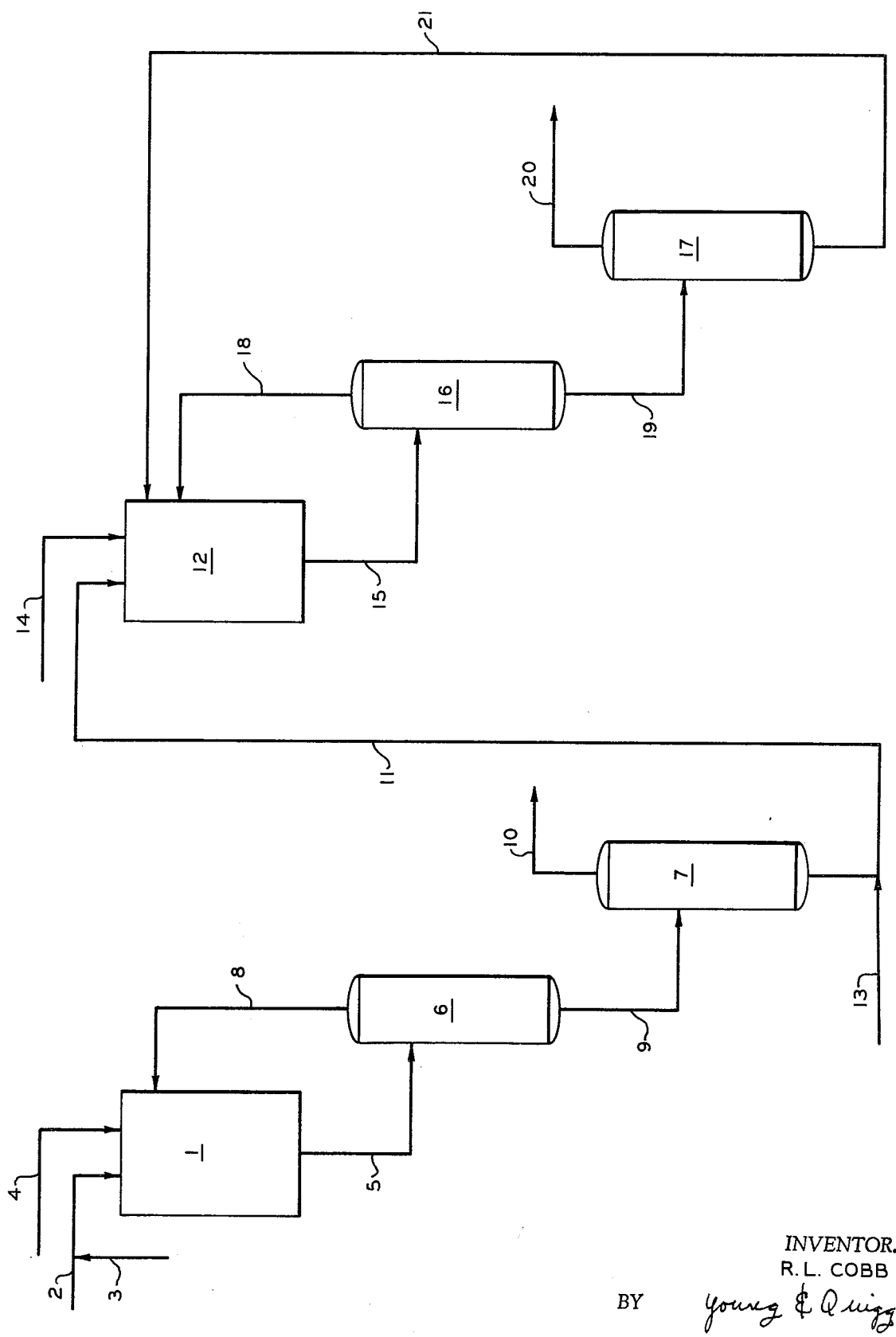
INVENTOR.
R.L. COBB
BY Young & Quigg
ATTORNEYS

CONVERSION OF LACTAMS TO ALKENENITRILES

This invention relates to the production of alkenenitriles from the corresponding lactams. It further relates to the production of alkenenitriles by treating the byproduct material formed during the production of alpha,omega-aminonitriles from the corresponding lactams. This invention still further relates to the ammonolysis of lactams wherein the byproduct thereof is subjected to catalytic cracking to produce mixed isomeric alkenenitriles.

Lactams are internal or cyclic amides which are converted to aminonitriles by ammonolysis, which is a cleavage reaction with ammonia. This reaction produces as a primary product the desired aminonitrile; however, it also produces a byproduct material hereinafter referred to as "polymer". It has been found that during the ammonolysis of lactams, 2 to 10 percent by weight or more of the lactam is converted to the above-referred-to polymer. The formation of polymer represents a loss or waste of the original lactam. It is desirable, however, to obtain maximum conversion of the lactam. Therefore, it is necessary, in order to maximize the commercial usefulness of the lactam conversion, to make maximum use of the byproduct polymer. Accordingly, by this invention the polymer is treated to convert it to useful unsaturated nitriles, specifically alkenenitriles.

The aminonitriles produced as a primary product in the first step of this invention are valuable chemicals since they are readily convertible to diamines or to other compounds useful as chemical intermediates.

The alkenenitriles produced as a primary product in the second step of this invention can be readily converted to unsaturated acids, unsaturated amines, or saturated acids, saturated amines, or saturated nitriles. The unsaturated nitriles produced from the polymer conversion can also be converted to polyfunctional materials by additions to the carbon-carbon double bond, for example, epoxynitriles, halonitriles and the like.

It is thus an object of my invention to provide a process for the production of aminonitriles and alkenenitriles from lactams.

It is another object of my invention to provide a process for the ammonolytic cleavage of lactams in the presence of a catalyst to the corresponding aminonitrile followed by the conversion of the byproduct formed by this cleavage to alkenenitriles in a catalytic cracking step.

Other objects, aspects and the several advantages of my invention will be apparent to one skilled in the art to which the invention most nearly pertains from a consideration of the following disclosure, figure, and claims.

According to my invention, there is provided a process for the conversion of lactams to the corresponding aminonitriles and alkenenitriles comprising contacting the lactam with ammonia in the presence of a cracking catalyst in a first reaction zone to form the corresponding aminonitrile and a byproduct polymeric material, and contacting the byproduct in the presence of a second cracking catalyst in a second reaction zone to form the alkenenitrile. The aminonitrile and alkenenitrile are both recovered as products of the process.

Further in accordance with my invention there is provided a two-step process comprising a first and a second reaction step. In the first reaction step a lactam solution is introduced into a first reaction zone wherein it is contacted with ammonia in the presence of a first cracking catalyst to produce the corresponding aminonitrile and a byproduct polymeric material. The aminonitrile and byproduct are separated in a first separation zone and the aminonitrile is recovered as a product of the process. The byproduct is delivered to the second reaction step. In the second reaction step the byproduct in solution form is introduced into a second reaction zone wherein, if desired, it can be contacted with ammonia in the presence of gamma-alumina, a second cracking catalyst, to produce isomeric alkenenitriles. The alkenenitriles are separated from unconverted byproduct in a second separation zone and the alkenenitriles are recovered as products of the process. The unconverted byproduct can then be recycled to the second reaction zone for further treatment.

My invention is further explained and can be readily understood by one skilled in the art from a consideration of the following disclosure and accompanying FIGURE, which is a flow diagram showing a process for converting lactams to alpha,omega-aminonitriles and alkenenitriles by contacting the lactams with ammonia in the presence of a first cracking catalyst in reaction zone 1 to thus produce the alpha,omega-aminonitriles and a byproduct polymer, and contacting the polymer from reaction zone 1 with ammonia in the presence of a second cracking catalyst in reaction zone 12 to thus produce the alkenenitrile.

The following description is in terms of the treatment of dodecanelactam to produce alpha,omega-aminododecanenitrile and isomeric dodecenenitriles, but the conditions, rates, catalysts and solvents pertaining to reaction zones 1 and 12 generally apply to the lactams (and the corresponding products) within the scope of this invention as will be hereinafter defined. The separation conditions in the following description pertaining to distillation zones 6, 7, 16 and 17 are specific to the dodecanelactam (and corresponding products) embodiment; however, it is well known in the distillation arts to adjust conditions of temperature and pressure to effect desired separation of particular materials and such would be the requirement where lactams other than dodecanelactam are employed.

Referring now to the FIGURE, dodecanelactam is introduced into reaction zone 1 via conduit 2. Prior to its introduction into reaction zone 1, the dodecanelactam is mixed with solvent which is introduced into conduit 2 upstream of reaction zone 1 via line 3. Sufficient solvent is introduced to produce a solution having a concentration in the range of 1.0 to 100, preferably 5 to 30, weight percent lactam by weight of solution. Ammonia is introduced into reaction zone 1 via line 4. Reaction zone 1 contains a catalyst which can be a silicon-containing compound such as an alkaline earth silicate, a mordenite or a synthetic zeolite generally referred to as a molecular sieve. Molecular sieves are described with some particularity in an article by D. W. Breck in the *Journal of Chemical Education*, Vol. 41, pages 678 and following, December 1964. The preferred catalyst is Union Carbide Molecular Sieve Type 3A, described in a paper by T. L. Thomas at the Sixth World Petroleum Congress, Frankfurt/Main (Union Carbide Corporation Bulletin F-2045). Various types of promoted catalysts are suitable, such as aluminum phosphate combined with or used for promoting alumina, silica, alkaline earth silicates, and the complex silicates, as just mentioned. Further, magnesium-aluminum-silicate-phosphate catalyst material precipitated onto a substrate which includes any of the silicas, aluminas, or substrates containing silica or alumina in admixture or combination can serve as a catalyst. The quantity of ammonia introduced into reaction zone 1 is based upon the molar ratio of ammonia to lactam. Thus, the lactam solution introduced into reaction zone 1 via line 2, and the ammonia introduced into reaction zone 1 via line 4, are sufficient to provide a molar ratio of ammonia to lactam in the range of 1 to 1000, preferably 10 to 50, moles of ammonia per mole of lactam. In addition, the lactam solution introduced into reaction zone 1 via line 2 is sufficient to provide a quantity of lactam in the range of 0.1 to 10, preferably 1.0 to 5.0, pounds of lactam per pound of catalyst per hour.

The solvents useful to dissolve the lactam include aromatics, such as benzene, toluene, xylene and the like; cycloaliphatics, such as cyclopentane, cyclohexane and the like; and cyclic ethers, such as tetrahydrofuran, tetrahydropyran and the like. Where dodecanelactam is being treated, the preferred solvent is toluene.

Reaction zone 1 is operated at a temperature in the range of 250° to 750° C., preferably at a temperature in the range of 350° to 500° C., and at a pressure in the range of 0 to 15,000 psig, preferably at a pressure in the range of 0 to 1500 psig.

Referring again to the FIGURE, the effluent from reaction zone 1 consisting of aminododecanenitrile along with unreacted dodecanelactam, solvent and ammonia as well as byproduct polymer is introduced into a first separation zone via line 5. In this embodiment, the first separation zone comprises distillation zone 6 and distillation zone 7, wherein the effluent from reaction zone 1 is introduced into distillation zone 6 via line 5. In distillation zone 6, a separation is effected whereby solvent and ammonia are separated from the aminonitrile, unreacted dodecanelactam and byproduct polymer. The solvent and ammonia exit distillation zone 6 via line 8, and they are recycled via line 8 and introduced into reaction zone 1. The aminododecanenitrile, unreacted dodecanelactam and byproduct polymer exit distillation zone 6 via line 9, and they are then introduced into distillation zone 7 via line 9. In distillation zone 7 a separation is effected between the aminonitrile, unreacted dodecanelactam, and the byproduct polymer, wherein the aminonitrile and dodecanelactam exit distillation zone 7 overhead via line 10 and further wherein the byproduct polymer, which can have occluded therein some dodecanelactam and aminododecanenitrile, exits from the bottom of distillation zone 7 via line 11. The combined aminonitrile and unreacted dodecanelactam are introduced via line 10 into a recovery system, not shown, for further processing such as distillation in which the product aminonitrile is separated from unreacted dodecanelactam. The unreacted dodecanelactam is then recycled to reaction zone 1.

The byproduct polymer produced in reaction zone 1 is introduced into reaction zone 12 via line 11. Prior to the introduction of polymer into reaction zone 12, it is mixed with solvent which is introduced into line 11 at a point upstream reacton zone 12 via line 13. Sufficient solvent is introduced to provide a solution of polymer in solvent to the extent of 2 to 40 weight percent polymer by weight of solution. Ammonia is introduced into reaction zone 12 via line 14. Reaction zone 12 contains a catalyst useful in converting the polymer into the desired alkenenitrile which, in this embodiment, can include one or more isomers of dodecanenitrile. The conversion of polymer to alkenenitrile in reaction zone 12 is not impeded even if the polymer introduced into reaction zone 12 has occluded therein some unreacted lactam and some aminonitrile. The rate at which the polymer solution is introduced into reaction zone 12 is based upon the quantity of catalyst contained in reaction zone 12. Thus, the solution of polymer and solvent is introduced into reaction zone 12 in an amount sufficient to provide 0.05 to 1.0 pound of polymer per pound of catalyst per hour. The rate at which ammonia is introduced is also dependent upon the quantity of catalyst in reaction zone 12. Thus, ammonia is introduced in an amount sufficient to provide 0.1 to 5 pounds of ammonia per pound of catalyst per hour. From the above-mentioned flow rates it is noted that the weight ratio of ammonia to polymer is in the range of 0.1 to 100 pounds ammonia per pound of polymer.

The catalyst employed in reaction zone 12 is gamma-alumina. A definitive discussion of gamma-alumina is found in an article by D. S. MacIver, H. H. Tobin and R. T. Barth in the *Journal of Catalysis*, Vol. 2, pages 485–497 (1963).

Solvents useful herein which are introduced via line 13 include aromatics such as benzene, toluene and the isomeric xylenes as well as cycloaliphatics such as cyclohexane, methylcyclopentane, ethylcyclohexane, and the like.

The ammonia and polymer contact each other in the presence of the catalyst in reaction zone 12 which operates at a reaction temperature in the range of 300° to 700° C., preferably 400° to 550° C., and at a pressure in the range of 0 to 2000 psig, preferably 0 to 1200 psig.

Again referring to the FIGURE, the effluent from reaction zone 12 containing the desired alkenenitrile as well as small amounts of aminonitrile previously occluded within the polymer mass, unconverted polymer, solvent, and ammonia is introduced via line 15 into a second separation zone comprising distillation zone 16 and distillation zone 17. The effluent from reaction zone 12, carried in line 15, is introduced into distillation zone 16 wherein solvent and ammonia are separated from the alkenenitrile, aminonitrile and unconverted polymer. The solvent and ammonia are removed overhead distillation zone 16 via line 18 and are recycled to reaction zone 12. The alkenenitrile, aminonitrile and unconverted polymer are removed from distillation zone 16 and carried via line 19 to distillation zone 17. In distilltion zone 17 there is effected a separation between the alkenenitrile, aminonitrile and unconverted polymer. The alkenenitrile and aminonitrile are removed overhead distillation zone 17 via line 20 as a product of the process. The combined alkenenitrile and aminonitrile are introduced via line 20 into a recovery system, not shown, for separation such as by distillation of the small amount of aminonitrile from the alkenenitrile. Dodecenenitrile yields range up to about 70 percent of theoretical. The unconverted polymer is removed from distillation zone 17 via line 21 and recycled to reaction zone 12.

The above description of my invention features the preferred embodiment wherein ammonia is introduced into reaction zone 12. However, in a second embodiment of my invention ammonia is not introduced into reaction zone 12. In the second embodiment the polymer does not contact the catalyst in the presence of ammonia. The polymer is cracked by merely contacting the catalyst. Other than the removal of ammonia from the second embodiment all other rates, pressures, temperature ranges and associated conditions as previously set out above are not changed.

The reaction in reaction zone 1 to which I have referred is an ammonialytic cleavage reaction which can be illustrated by the following:

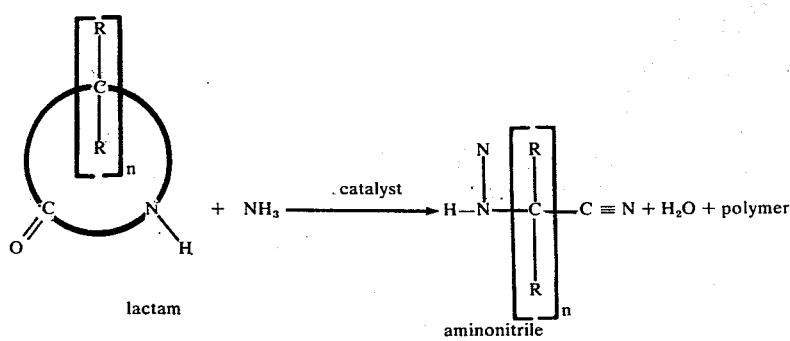

Various substituents can be on the carbons of the lactam ring, as shown by the R symbols in the formulas given above. Each R can be hydrogen, alkyl, cycloalkyl, aryl or combinations thereof such as alkylaryl or arylalkyl and the like, and can have in the range of from 1 to about 8 carbon atoms provided that not more than 10 carbon atoms are contained in the total of R groups per lactam molecule. The n is an integer indicating the number of

units and can range from about 3 to 18, inclusive, and the R groups can differ between

units. Examples of lactams within the scope of this invention include 12-aminododecanoic acid lactam (dodecanelactam), 4-aminobutyric acid lactam, 14-amino-3-butyl-8-methyltetradecanoic acid lactam, 18-amino-5-(3,5-dimethylphenyl)octadecanoic acid lactam, and 9-amino-5-cyclohexylnonanoic acid lactam.

EXAMPLE

A 25 weight percent solution of dodecanelactam in toluene was introduced into a reactor which was operating at 450° C. and 1200 psig and which had therein as a catalyst type 3A molecular sieve. The dodecanelactam solution was introduced into the reactor at a rate sufficient to provide 4.2 pounds of dodecanelactam per pound of catalyst per hour. Also introduced into the reactor was ammonia at the rate of 10.9 pounds of ammonia per pound of catalyst per hour. Thus the ratio of ammonia to dodecanelactam was about 28.4 moles ammonia per mole of dodecanelactam. The dodecanelactam and ammonia reacted in the presence of the catalyst in the reactor to produce a product mixture consisting of approximately 15 percent unreacted dodecanelactam, approximately 75 percent alpha,omega-aminododecanenitrile and approximately 9 percent of a material which consisted of 87 percent by weight byproduct polymer and 13 percent by weight occluded dodecanelactam and alpha,omega-aminododecanenitrile. The reaction product also contained a trace quantity of dodecenenitriles including one or more isomers.

The byproduct polymer (and occluded matter) was separated from the above-described reaction product by distillation means and thereafter the polymer was dissolved in toluene. The resulting solution, which was 25 percent by weight of the said dissolved polymer, was divided into four portions and each portion was passed over gamma-alumina as a catalyst wherein said polymer was converted to isomeric dodecenenitriles. The conditions and results of the three runs were as follows:

| Run No. | Temp., ° C. | Pressure, psig | Lbs Polymer/ Lb Catalyst/ Hour | Lbs Ammonia/ Lb Catalyst/ Hour | Wt.% Polymer Converted to Dodecenenitrile |
|---|---|---|---|---|---|
| 1 | 360 | 440 | 0.25 | 0.6 | 5.2 |
| 2 | 460 | 430 | 0.25 | 0.6 | 53.1 |
| 3 | 500–525 | 460–470 | 0.25 | 0.6 | 68.1 |
| 4 | 490–500 | 0 | 0.25 | 0 | 64.3 |

Reasonable variations and modifications can be made in the process of my invention, which is the catalytic cracking of polymers formed by the interaction of lactams with ammonia, without departing from the spirit or scope thereof.

Having described my invention, that which is claimed is:

1. A process for the production of alkenenitriles from the polymer byproduct resulting from the ammonolysis of one or more lactams to form the corresponding alpha,omega-aminonitrile which comprises treating said polymer byproduct with ammonia in a reaction zone in the presence of a gamma-alumina catalyst at a temperature in the range of 300° to 700° C. and at a pressure in the range of 0 to 2000 psig whereby said polymer byproduct is converted to the corresponding alkenenitrile and thereafter recovering the resulting alkenenitrile as a product of the process.

2. The process of claim 1 wherein said polymer is the byproduct of the ammonolysis of dodecanelactam and said alkenenitrile is dodecenenitrile.

3. A process for the production of alkenenitriles from lactams which comprises treating at least one lactam with ammonia in a first reaction zone containing a cracking catalyst and which is maintained at a temperature in the range of 250° to 750° C. and at a pressure in the range of 0 to 15,000 psig whereby a first reaction product is formed which consists essentially of the aminonitrile corresponding to said lactam and a polymer byproduct; separating said polymer byproduct from said aminonitrile; thereafter treating said polymer byproduct with ammonia in a second reaction zone containing gamma-alumina and which is maintained at a temperature in the range of 300° to 700° C. and at a pressure in the range of 0 to 2,000 psig whereby said polymer byproduct is converted to the corresponding alkenenitrile; and thereafter recovering the resulting alkenenitrile as a product of the process.

4. A process according to claim 3 wherein said lactam is dodecanelactam and said alkenenitrile is dodecenenitrile.

* * * * *